United States Patent
Pavlatos et al.

(10) Patent No.: US 11,443,855 B2
(45) Date of Patent: Sep. 13, 2022

(54) SECURE DISPERSED NETWORK FOR IMPROVED COMMUNICATIONS BETWEEN HEALTHCARE INDUSTRY PARTICIPANTS

(71) Applicant: PatientMD, Inc., Chicago, IL (US)

(72) Inventors: Christ Pavlatos, Chicago, IL (US); Anirban Majumdar, Chicago, IL (US)

(73) Assignee: PatientMD, Inc., Chicago, IL (US)

( * ) Notice: Subject to any disclaimer, the term of this patent is extended or adjusted under 35 U.S.C. 154(b) by 0 days.

(21) Appl. No.: 17/270,097

(22) PCT Filed: Aug. 21, 2019

(86) PCT No.: PCT/US2019/047592
§ 371 (c)(1),
(2) Date: Feb. 22, 2021

(87) PCT Pub. No.: WO2020/041528
PCT Pub. Date: Feb. 27, 2020

(65) Prior Publication Data
US 2021/0174972 A1    Jun. 10, 2021

Related U.S. Application Data

(60) Provisional application No. 62/767,057, filed on Nov. 14, 2018, provisional application No. 62/727,023, filed on Sep. 5, 2018, provisional application No. 62/721,096, filed on Aug. 22, 2018, provisional application No. 62/720,699, filed on Aug. 21, 2018, provisional application No. 62/720,477, filed on Aug. 21, 2018.

(51) Int. Cl.
| | | |
|---|---|---|
| *H04L 29/00* | (2006.01) |
| *G16H 80/00* | (2018.01) |
| *G16H 70/00* | (2018.01) |
| *G16H 10/60* | (2018.01) |
| *H04L 9/32* | (2006.01) |

(52) U.S. Cl.
CPC ............ *G16H 80/00* (2018.01); *G16H 10/60* (2018.01); *G16H 70/00* (2018.01); *H04L 9/3213* (2013.01); *H04L 2209/38* (2013.01); *H04L 2209/56* (2013.01)

(58) Field of Classification Search
CPC ........ G16H 80/00; G16H 10/60; G16H 70/00; G16H 40/67; H04L 9/3213; H04L 2209/56; H04L 2209/38
See application file for complete search history.

(56) References Cited

U.S. PATENT DOCUMENTS

| | | | |
|---|---|---|---|
| 10,255,458 B2 * | 4/2019 | Aunger | G06F 21/6245 |
| 2003/0163488 A1 | 8/2003 | Kloos et al. | |
| 2015/0348169 A1 * | 12/2015 | Harris | G06Q 30/0633 705/26.8 |
| 2017/0279774 A1 | 9/2017 | Booz et al. | |
| 2017/0300627 A1 | 10/2017 | Giordano et al. | |
| 2017/0372300 A1 * | 12/2017 | Dunlevy | G16Z 99/00 |
| 2018/0053161 A1 * | 2/2018 | Bordash | G06Q 20/382 |
| 2018/0060496 A1 | 3/2018 | Bulleit et al. | |
| 2018/0117447 A1 | 5/2018 | Tran et al. | |
| 2018/0176727 A1 * | 6/2018 | Williams | A61B 5/747 |
| 2018/0211058 A1 * | 7/2018 | Aunger | H04L 63/0428 |
| 2019/0228461 A1 * | 7/2019 | Domokos | G06Q 30/0613 |
| 2019/0237169 A1 * | 8/2019 | Culver | G06Q 30/0207 |

OTHER PUBLICATIONS

Patel, Vishal. "A framework for secure and decentralized sharing of medical imaging data via blockchain consensus." Health Informatics Journal. 2019, vol. 25(4) 1398-1411. First Published Apr. 25, 2018. (Year: 2018).*
International Search Report and Written Opinion for corresponding PCT/US19/47592 (dated Dec. 17, 2019), 16 pages.

* cited by examiner

*Primary Examiner* — Don G Zhao
(74) *Attorney, Agent, or Firm* — Incubate IP; Randy R. Micheletti

(57) ABSTRACT

The present disclosure provides blockchain computing systems and methods of using same.

16 Claims, No Drawings

SECURE DISPERSED NETWORK FOR IMPROVED COMMUNICATIONS BETWEEN HEALTHCARE INDUSTRY PARTICIPANTS

PRIORITY CLAIMS

This application is a national stage entry of International Patent Application Ser. No. PCT/US19/47592, filed on Aug. 21, 2019, which claims priority to: (i) U.S. Provisional Patent Application Ser. No. 62/720,477, filed Aug. 21, 2018; (ii) to U.S. Provisional Patent Application Ser. No. 62/720,699, filed Aug. 21, 2018; (iii) to U.S. Provisional Patent Application Ser. No. 62/721,096, filed Aug. 22, 2018; (iv) to U.S. Provisional Patent Application Ser. No. 62/727,023, filed Sep. 5, 2018; and (v) to U.S. Provisional Patent Application Ser. No. 62/767,057, filed Nov. 14, 2018, the entire contents of each of which are incorporated herein by reference and relied upon.

BACKGROUND

Current systems and platforms do not allow participants in the healthcare industry to adequately monitor or incentivize healthcare patients to maintain or improve their health and well-being. For example, currently available systems and platforms do not enable patients, doctors, business, and government agencies to collaborate in a transparent, immutable and trusted way to compensate patients for making good medical choices.

The present disclosure describes systems and methods that meet that need.

SUMMARY

The present disclosure relates generally to systems (e.g., digital platforms) that (1) bring all parties involved in receiving, providing, monitoring, and reimbursing healthcare services (e.g., patients, doctors, businesses and government) together; (2) incentivize each party to share activities and information; (3) monitor the activities and information sharing through smart contracts; and (4) compensate patients for acting in ways consistent with good medical/health choices and good economic theories.

In one embodiment, the present disclosure provides a computer-based method comprising: providing a blockchain computing system that stores and maintains a blockchain ledger, wherein the blockchain computing system hosts: (i) an encrypted electronic health record associated with a patient, and (ii) a smart contract that uses the blockchain ledger to verify blockchain transactions with the smart contract; providing an off-chain computer system comprising: a third-party module configured to enable a third party to generate a smart contract to incentivize a patient to complete a task (e.g., perform an action or purchase a product or service), wherein the smart contract is published to the blockchain ledger, a patient module configured to enable the patient to: (i) selectively grant access to at least a portion of the encrypted electronic health record associated with the patient to an authorized doctor or an authorized business, and (ii) generate a request to execute the smart contract, and a doctor module configured to enable the authorized doctor to: (i) access the encrypted electronic health record, and (ii) generate a request to publish a block to the blockchain ledger, wherein the block includes updated medical information about the patient; receiving, by the blockchain computing system, a request by the patient to execute the smart contract via a blockchain transaction; verifying, by the blockchain computing system, that the blockchain transaction satisfies the smart contract; and transferring, if the blockchain transaction satisfies the smart contract, a blockchain token to a digital wallet associated with the patient.

In another embodiment, the present disclosure provides a system comprising: a blockchain computing system configured to: (i) store and maintain a blockchain ledger, and (ii) host a smart contract that uses the blockchain ledger to verify blockchain transactions with the smart contract; and an off-chain computer system configured to: (i) receive a request from the blockchain computing system associated with the smart contract, (ii) enable a third party to generate a smart contract to incentivize a patient to complete a task (e.g., perform an action or purchase a product or service), wherein the smart contract is published to the blockchain ledger, (iii) enable the patient to: (a) selectively grant access to at least a portion of the encrypted electronic health record associated with the patient to an authorized doctor, and (b) generate a request to execute the smart contract, and (iv) enable the authorized doctor to: (a) access the encrypted electronic health record, and (b) generate a request to publish a block to the blockchain ledger, wherein the block includes updated medical information about the patient.

In other embodiments, the present disclosure provides a method of incentivizing a patient to perform a task, the method comprising: providing a blockchain computing system that stores and maintains a blockchain ledger, wherein the blockchain computing system hosts a smart contract that uses the blockchain ledger to verify blockchain transactions with the smart contract; providing an off-chain computer system comprising: a third-party module configured to enable a third party to generate a smart contract to incentivize a patient to perform a task, wherein the smart contract is published to the blockchain ledger, a patient module configured to enable the patient to view a published smart contract, and a doctor module configured to enable a doctor to: generate a smart contract to incentivize a patient to perform a task, wherein the smart contract is published to the blockchain ledger; generating, by the patient module, the third-party module or the doctor module, a request to execute the published smart contract; receiving, by the blockchain computing system, a request by the patient to execute smart contract via a blockchain transaction; verifying, by the blockchain computing system, that the blockchain transaction satisfies the smart contract; and transferring, if the blockchain transaction satisfies the smart contract, a blockchain coupon to the patient.

In a further embodiment, the present disclosure provides a blockchain coupon comprising: a financial value that represents a discount off of a purchase price of a service or product available for purchase on a blockchain computing system; and a request that, upon redemption by a patient, causes an off-chain computing system to execute a smart contract hosted by the blockchain computing system, wherein, upon verification of the smart contract, the smart contract causes transfer of the purchase price less the financial value from a digital wallet associated with the patient to a digital wallet associated with a provider of the service or product.

In another embodiment, the present disclosure provides a method of incentivizing patient behavior, the method comprising: providing a blockchain computing system that stores and maintains a blockchain ledger, wherein the blockchain computing system hosts a smart contract that uses the blockchain ledger to verify blockchain transactions with the smart contract; providing an off-chain computer system comprising: a third-party module configured to enable a third party to generate a smart contract to incentivize a patient to perform a task, wherein the smart contract is published to the blockchain ledger, and a patient module configured to generate a request to execute the smart contract; generating, by the patient module, a request to execute the published smart contract; receiving, by the blockchain computing system, the request by the patient to execute the smart contract via a blockchain transaction; verifying, by the blockchain computing system, that the blockchain transaction satisfies the smart contract; and transferring, if the blockchain transaction satisfies the smart contract, a health savings account token to a digital wallet associated with the patient.

In a further embodiment, the present disclosure provides a digital wallet comprising a health savings account token or fraction thereof.

In another embodiment, the present disclosure provides a method of recruiting patients for a medical study, the method comprising: providing a blockchain computing system that stores and maintains a blockchain ledger, wherein the blockchain computing system hosts: (i) an encrypted health record associated with each of a plurality of patients, and (ii) a smart contract that uses the blockchain ledger to verify blockchain transactions with the smart contract; providing an off-chain computer system comprising: a third-party module configured to enable a third party to generate a smart contract to incentivize a patient to complete a task (e.g., perform an action or purchase a product or service), wherein the smart contract is published to the blockchain ledger, and a patient module configured to enable the patient to: (i) selectively grant access to at least a portion of the encrypted health record associated with the patient to the third party, and (ii) generate a request to execute the smart contract; receiving, by the blockchain computing system, a request by the patient to execute the smart contract via a blockchain transaction; verifying, by the blockchain computing system, that the blockchain transaction satisfies the smart contract; and transferring, if the blockchain transaction satisfies the smart contract, a blockchain token to a digital wallet associated with the patient.

In a further embodiment, the present disclosure provides a stable healthcare blockchain token, wherein one healthcare blockchain token comprises a value directly proportional to a value of one unit of a predetermined fiat currency.

In another embodiment, the present disclosure provides a stable healthcare blockchain token, wherein one healthcare blockchain token comprises a value directly proportional to a value of one unit of a predetermined cryptocurrency.

DETAILED DESCRIPTION

The present disclosure provides blockchain computing systems and methods of using same.

Generally, the blockchain computing systems of the present disclosure enable healthcare patients and their caregivers ("patients"), healthcare service providers such as doctors, nurses, nurse practitioners, clinics, and hospitals ("doctors"), and non-healthcare entities like insurance companies, clinical research organizations, and healthcare product merchants ("third parties") to communicate with each other and conduct highly efficient secure and privacy regulation-compliant transactions with each other through the use of smart contracts published to the blockchain ledger associated with the blockchain computing system, the satisfaction of which may be automatically verified by the blockchain computing system thus providing trustworthy, economically efficient interactions between these heretofore largely siloed healthcare industry participants. In addition, the use of smart contracts as disclosed herein enables healthcare industry participants of all types (including patients) to incentivize desirable conduct by other healthcare industry participants in a variety of ways that have, until now, been impossible or significantly impractical.

1. Health Mining Blockchain Systems

Incentivizing health care consumers (e.g., patients) to improve—or even maintain—good health remains a challenge, especially for employers, insurance companies, health care professionals (e.g., doctors), and national/state/local government agencies. For example, no platform accessible to patients, doctors, governments, and third-party businesses (e.g., insurance companies) for monitoring patient health activity and health information in order to incentivize (e.g., compensate) healthy patient choices has heretofore existed. The present disclosure provides a convenient platform through which any of those actors may provide economic and/or social incentives to health care consumers, to doctors, or to third parties.

In general, health care consumers (e.g., patients) may be incentivized in a method of the present disclosure by offering a blockchain token through the use of a smart contract. Satisfaction of the smart contract generally requires behavior by the health care consumer (e.g., patient) evidencing good health/medical and/or economic behavior.

A. Blockchain Computing System

Systems and methods of the present disclosure include a computer system on a distributed network, such as a blockchain computing system. The blockchain computing system stores and maintains a blockchain ledger, and hosts (at least): an encrypted electronic health record associated with a patient, and a smart contract for incentivizing the patient to take a certain action or purchase a certain service. The blockchain ledger verifies blockchain transactions with the smart contract and, if the smart contract is satisfied by the patient's action or purchase, the blockchain computing system transfers an economic incentive (e.g., a blockchain token) to the patient's digital wallet.

B. Off-Chain Computer System

An off-chain computer system interacts with the blockchain system, and includes (at least): a third-party module, a patient module, and a doctor module.

i. Third-Party Modules

The third-party module is configured to allow a third party to generate a smart contract to be published to the blockchain ledger. In some embodiments, the smart contract includes instructions to automatically transfer an economic incentive (e.g., a blockchain token) to the patient, but only if the patient performs a task or purchases a product or service required by the smart contract. In some embodiments, the smart contract includes an expiration date that prevents the transfer of the economic incentive to the patient if the task is performed or if the purchase is made after the expiration date. In some embodiments, the smart contract includes a performance deadline that prevents transfer of the economic incentive to the patient if a purchased service is not provided to the patient by the performance deadline. The economic incentive may be in any form capable of being automatically transferred to the patient, such as a blockchain token transferred to the patient's digital wallet. The product required to be purchased by a smart contract may be a health-related product, such as a health monitoring device, an over-the-counter medication, a prescribed pharmaceutical, an exercise device, a health club membership, an orthopedic product (e.g., a joint brace or corrective footwear), healthy food, or any other product designed to improve a patient's health or maintain a patient's existing good health. The task to be performed may be a health-related task, such as scheduling an appointment with a health care provider, attending a scheduled appointment with a health care provider, retrieving a purchased prescribed medication, test, or treatment, watching a video presented by or on behalf of the third party, or playing a game sponsored by the third party. Thus, the smart contract creates an economic incentive for the patient to complete a task, purchase a product, or purchase and receive a service related to improving or maintaining the patient's health. In some embodiments, the third-party module is configured to prevent a third party using the third-party module from accessing the encrypted electronic health record. In some embodiments, the third-party module is configured to prevent a third party using the third-party module from accessing the encrypted electronic health record, unless the third party is a verified healthcare insurance provider of which the patient is or was a member. In some embodiments, the third-party module is configured to prevent a third party using the third-party module from accessing the encrypted electronic health record, unless the third party is a verified life insurance provider from which the patient has or is actively seeking a life insurance policy. In some embodiments, the third-party module is configured to prevent a third party using the third-party module from accessing the encrypted electronic health record, unless the third party is a verified contract research organization and the patient has elected to enroll in (or to be considered for) a clinical study.

In general, the third-party module does not permit a third party to access any form of a patient record (e.g., an encrypted electronic health record) without the patient granting access to the third party. In some embodiments, the patient is compensated for granting access to his or her encrypted electronic health record to the third party, for example by causing the patient module to transmit a request to the blockchain computing system (e.g., acting as an inbound blockchain oracle) to execute a smart contract that causes the blockchain computing system to transfer an economic incentive (e.g., a token, cryptocurrency, or a blockchain coupon) to the patient's digital wallet. In some embodiments, the economic incentive is transferred to the patient's digital wallet from the third party's digital wallet. In some embodiments, the third party is an insurance provider. In some embodiments, the third party is a clinical research organization.

In some embodiments, the smart contract includes instructions to automatically transfer an economic incentive (e.g., a blockchain token) to the doctor, but only if the doctor performs a task, purchases a product or service, or sells a product or service required by the smart contract. In some embodiments, the smart contract includes an expiration date that prevents the transfer of the economic incentive to the doctor if the task is performed, if the purchase is made, or if the sale is made after the expiration date. In some embodiments, the smart contract includes a performance deadline that prevents transfer of the economic incentive to the doctor if a sold service is not provided to a patient by the performance deadline. The economic incentive may be in any form capable of being automatically transferred to the doctor, such as a blockchain token transferred to the patient's digital wallet.

In some embodiments, the third-party module is configured to enable a third party to communicate via encrypted message (e.g., e-mail, text (SMS), or push notification) with a patient using the patient module, and/or with a doctor using the doctor module. In some embodiments, the encrypted message is published to the blockchain ledger as a block with encryption such that only the sender of the encrypted message and the recipient of the encrypted message can access the text of the encrypted message. In some embodiments, the encrypted message is published to the blockchain ledger as a block with encryption to provide non-repudiation to the third party and the patient.

In some embodiments, the third-party module is configured to enable a media provider (e.g., a doctor or any third party) to contribute media content (e.g., audio, video, and/or text) to be offered to patients, doctors, and/or third parties through the patient module, the doctor module, and/or the third-party module (respectively), and to optionally receive an economic incentive (e.g., in the form of a blockchain token transferred to a digital wallet associated with the media provider) for contributing the media content and/or for views of the content by patients, by doctors, and/or by third parties. In some embodiments, the media content is hosted by the off-chain computing system and viewable to the patient via the patient module.

In some embodiments, the third-party module is configured to enable a third party (e.g., a governmental organization or a non-governmental health organization) to create a smart contract specifying a protocol (e.g., a treatment protocol and/or a diagnostic protocol) for identifying, treating, and/or managing a disease or disorder associated with a patient. For example, the protocol may specify one or more steps of an evidence-based medical protocol for diagnosing, treating, or managing a disease or disorder. The doctor may, via the doctor module, indicate that he or she performed the one or more steps specified in the smart contract for a patient. The doctor module transmits a request to the blockchain computing system (e.g., acting as an inbound blockchain oracle) to execute the smart contract. Upon verification by the blockchain computing system that all required steps of the smart contract were performed, the blockchain computing system executes the smart contract. In some embodiments, execution of the smart contract includes publishing a block to the blockchain ledger that updates the patient's electronic health record to indicate that the protocol specified in the smart contract were performed by the doctor. In some embodiments, the smart contract includes an economic incentive (e.g., a token and/or a blockchain coupon) that, upon execution of the smart contract, causes the blockchain computing system to transfer the economic incentive to the digital wallet of the doctor.

In some embodiments, the economic incentive is transferred to the digital wallet of the patient. In some embodiments, the economic incentive is transferred to the digital wallet of a third party (e.g., an insurance provider, a federal or state government agency, an employer, or a health care facility such as a clinic or a hospital).

ii. Patient Modules

The patient module is configured to enable the patient to (at least): (i) selectively grant access to at least a portion of the encrypted electronic health record associated with the patient to an authorized doctor, and (ii) generate a request to execute the smart contract.

Providing selective access to at least a portion of the patient's encrypted electronic health record to, for example, a doctor, a nurse, a healthcare service provider (e.g., a doctor group, clinic, or hospital), a health insurance company, or a life insurance company, improves the patient's control over who is able to read portions of the patient's encrypted electronic health record, and prevents unauthorized access of the patient's encrypted electronic health record by anyone to whom the patient has not granted access. The patient module may be configured to enable the patient to grant access to all of the patient's encrypted electronic health record, or to only a selected portion of the patient's encrypted electronic health record. In some embodiments, the patient may grant access to the patient's encrypted electronic health record (or a portion thereof) in response to a request for access provided to the patient by a doctor or by a third party, for example through an encrypted message sent by the doctor or third party to the patient. In some embodiments, the patient may grant access to the patient's encrypted electronic health record (or a portion thereof) in response to a smart contract published to the blockchain ledger by a doctor or by a third party.

The patient module also enables the patient to generate a request to execute the smart contract (e.g., to redeem a smart contract by demonstrating performance of the required task or purchase of the required product or service). For example, if a smart contract requires the patient to attend a scheduled appointment with a health care provider, the patient module may enable the patient to "check in" at the health care provider's location (e.g., by selecting a "check in" button within the patient module's graphical user interface). By checking in through the patient module, the patient module transmits information about the patient's check-in event (e.g., date, time, address or GPS-derived location) to the blockchain computing system (e.g., acting as an inbound blockchain oracle). If the information about the patient's check-in event matches information associated with a scheduled appointment for that patient stored in the blockchain ledger (e.g., through a smart contract specifying the date, time, and location of the patient's scheduled appointment), then the blockchain computing system verifies the patient's attendance at the scheduled appointment. In embodiments wherein the scheduled appointment is published to the blockchain ledger as a smart contract, the blockchain computing system verifies satisfaction of the smart contract if the patient's check-in information matches the scheduled appointment data stored in the published smart contract.

In other embodiments, the patient module may enable the health care provider to confirm the patient's attendance at the scheduled appointment by, for example, prompting the health care provider to enter unique identifying information associated with the health care provider into the patient module, for example on the patient's computing device (e.g., smart phone or cellular-enabled tablet). In such embodiments, the patient's attendance at the scheduled appointment is verified by the blockchain computing system if the unique identifying information associated with the health care provider that is entered into the patient module matches the health care provider identifying information stored in the blockchain ledger (e.g., in a smart contract).

In some embodiments, the patient module enables the patient to schedule an appointment with a health care provider (e.g., a doctor, clinic, or hospital). In some embodiments, the patient module is configured to enable the patient to view a patient appointment schedule established by a doctor via the doctor module, or by a third party via the third-party module. In some embodiments, the patient module is configured to enable the patient to pre-pay an insurance co-pay and/or a portion or all of the cost of the service associated with an appointment to be scheduled. In some embodiments, the pre-payment is transferred without the use of a token or cryptocurrency (e.g., through a non-blockchain payment provider such as PayPal, Venmo, or a credit card/debit card payment processor). In other embodiments, the pre-payment is transferred via a smart contract that, when executed, causes a token or cryptocurrency to transfer from the patient's digital wallet to the doctor's digital wallet or to a third party's digital wallet.

In some embodiments, the patient module enables the patient to receive a health care-related service remotely (e.g., "telemedicine"). In some embodiments, the blockchain computing system or the off-chain computing system may enable a private audio, video, and/or text message-based conversation between the patient using the patient module and the health care service provider using the doctor module or the third party module. The private conversation channel may be a video chat window (e.g., enabling exchange of audio and video between the patient and the mental health counselor), an audio chat (e.g., enabling exchange of audio only between the patient and the mental health counselor), or a text chat (e.g., enabling exchange of text-based messages only between the patient and the mental health counselor). In some embodiments, the patient is incentivized to participate in a telemedicine event by, for example, a smart contract that, upon execution, causes a token or cryptocurrency to be transferred into the patient's digital wallet. In some embodiments, the doctor is incentivized to participate in a telemedicine event by, for example, a smart contract that, upon execution, causes a token or cryptocurrency to be transferred into the doctor's digital wallet. In some embodiments, the token or cryptocurrency is transferred to the patient's digital wallet from the digital wallet of the doctor providing the telemedicine service. In other embodiments, the token or cryptocurrency is transferred to the patient's digital wallet from the digital wallet of a third party.

Patients can be incentivized to view educational videos provided by third parties. In some embodiments, a smart contract from the third party providing the educational video offers a blockchain token to the patient for viewing the educational video. Once the patient views the video (e.g., via the off-chain patient module), the patient module transmits a request to the blockchain computing system (e.g., acting as an inbound blockchain oracle) to execute the smart contract. Upon verification by the blockchain computing system that the patient viewed the video, the blockchain computing system causes a blockchain token, a blockchain coupon, or cryptocurrency to the digital wallet of the patient.

In some embodiments, the patient module enables the patient to purchase products and/or services from doctors or third parties using tokens in the patient's digital wallet, earned by the patient upon execution of one or more smart contracts hosted by the blockchain computing system. In some embodiments, a token in the patient's digital wallet is associated with no restrictions (e.g., temporal restrictions or restrictions on the product or service that can be purchased with the token, or source from which the product or service can be purchased with the token). In other embodiments, a token in the patient's digital wallet contains a restriction (e.g., a temporal restriction or a restriction on the product or service that can be purchased with the token, or source from which the product or service can be purchased with the token). In some embodiments, the restriction(s) associated with the token is encoded in a smart contract specifying, for example, an expiration date, a product type (e.g., SKU), and/or a service type (e.g., a Common Procedural Technology ("CPT") code and/or a Healthcare Common Procedure Coding System ("HCPCS") code) limiting redemption of the token by the patient. In such embodiments, the restriction(s) associated with the token are perpetual, and remain restrictions with that token in perpetuity. In other such embodiments, the restriction(s) associated with the token expire after a predetermined period of time (e.g., one year), after which time the token may be used to purchase (or to reduce the purchase price of) any product or service available on the electronic marketplace. In some embodiments, the restriction is a source restriction that is a temporal restriction limiting use of the token to purchase only products or services offered by the third-party provider of the token. For example and without limitation, if Third Party A provides Patient A with a token that includes a one-year source restriction, Patient A will only be able to use the token to purchase products or services offered by Third Party A for the one-year period specified in the token (e.g., one year from the date the token is initially transferred to Patient A's digital wallet, or one year from the date Third Party A first offered the token to any patient satisfying the requirements of the associated smart contract). After the one-year temporal restriction expires, Patient A may use the token to purchase any products or services, whether offered by Third Party A or not.

Unlike typical blockchain-based tokens, the value of which are perfectly fungible within any given platform, tokens associated with the present disclosure that have one or more restrictions on their use are not fungible. A token exchange marketplace is configured in some embodiments to enable patients to buy, sell, or trade tokens with other patients. In some embodiments, the token exchange marketplace is viewable and executable via the off-chain computing system (e.g., via the patient module, the doctor module, and/or the third-party module), and records of the executed token exchange transactions are maintained via a blockchain ledger operated by the blockchain computing system. For example, a token including a restriction limiting its use for one year to purchasing only products or services from Third Party A may have relatively little value to Patient A, but may have relatively high value to Patient B, who may desire to purchase a product or service from Third Party A before the one-year use restriction requires. Using the patient module, Patient A may sell the token to Patient B for cryptocurrency or fiat cash, or may trade the token to Patient B for an unrestricted token or a token with different restriction(s). Upon completion of the off-chain sale or trade, the patient module may transmit a request to the blockchain computing system (e.g., acting as an inbound blockchain oracle) to transfer the restricted token from Patient A's digital wallet to Patient B's digital wallet and to transfer the cryptocurrency, unrestricted token, or differently-restricted token from Patient B's digital wallet to Patient A's digital wallet. In some embodiments, a temporal restriction associated with a token may increase, decrease, or remain the same upon transfer of the token from one patient to another patient. In some embodiments, a transaction fee associated with the sale or trade of tokens between patients may be transferred to the digital wallet associated with the blockchain computing system operator.

In some embodiments, the patient module enables the patient to communicate, anonymously, with other patients through their patient modules, with doctors using the doctor module, and/or with third parties using the third-party module, to learn about specific medical conditions, healthy activities, and the like. In some embodiments, the communications between users occurs off-chain. In some embodiments, communications between users are published to the blockchain ledger (e.g., after a communication is sent off-chain between two or more users) as an archival record of the communications, for non-repudiation purposes.

iii. Doctor Modules

The doctor module is configured to enable a health care services provider (e.g., a doctor, a nurse, a nurse practitioner, a physician's assistant, a clinic, or a hospital, all referred to collectively herein as a "doctor") to (at least): (i) access the encrypted electronic health record associated with a patient who has granted access to the doctor, and (ii) generate a request to publish a block to the blockchain ledger, wherein the block includes updated medical information about the patient.

The doctor module may, in some embodiments, prompt a patient to grant access to the patient's encrypted electronic health record (or a portion thereof) by publishing a smart contract to the blockchain ledger. The blockchain computing system may then transmit a message to the patient via the patient module to accept or deny the access request from the doctor. If the patient accepts the doctor's request, the patient module transmits a response to the smart contract (e.g., acting as an inbound blockchain oracle) that is verified by the blockchain computing system, for example by confirming that unique identifying information transmitted from the patient module matches unique patient-identifying information in the smart contract. When the blockchain computing system verifies the patient response to the smart contract, the blockchain computing system then enables the doctor to view the patient's encrypted electronic health record, or the portion thereof that the patient has granted access, through the doctor module.

In some embodiments, the doctor module may enable the doctor to confirm the patient's attendance at the scheduled appointment by, for example, prompting the doctor to enter unique identifying information associated with the doctor (e.g., a unique user name and password, or a bar code/QR code scan) into the doctor module, for example on a computing device (e.g., smart phone or cellular-enabled tablet) associated with the doctor. In such embodiments, the patient's attendance at the scheduled appointment is verified by the blockchain computing system if the unique identifying information associated with the doctor that is entered into the doctor module matches the doctor identifying information stored in the blockchain ledger (e.g., in a smart contract).

In some embodiments, the doctor module enables the patient to schedule an appointment with the doctor. In some embodiments, the doctor module is configured to enable the doctor to establish an appointment schedule that may be viewed by a patient using the patient module. In some embodiments, the doctor module is configured to enable the patient to pre-pay an insurance co-pay and/or a portion or all of the cost of the service associated with an appointment to be scheduled to the doctor. In some embodiments, the pre-payment is transferred without the use of a token or cryptocurrency (e.g., through a non-blockchain payment provider such as PayPal, Venmo, or a credit card/debit card payment processor). In other embodiments, the pre-payment is transferred via a smart contract that, when executed, causes a token or cryptocurrency to transfer from the patient's digital wallet to the doctor's digital wallet.

In some embodiments, the doctor module enables the doctor to provide a health care-related service remotely (e.g., "telemedicine"). In some embodiments, the blockchain computing system or the off-chain computing system may enable a private audio, video, and/or text message-based conversation between the patient using the patient module and the doctor using the doctor module. The private conversation channel may be a video chat window (e.g., enabling exchange of audio and video between the patient and the mental health counselor), an audio chat (e.g., enabling exchange of audio only between the patient and the mental health counselor), or a text chat (e.g., enabling exchange of text-based messages only between the patient and the mental health counselor). In some embodiments, the doctor is incentivized to participate in a telemedicine event by, for example, a smart contract that, upon execution, causes a token or cryptocurrency to be transferred into the doctor's digital wallet. In some embodiments, the token or cryptocurrency is transferred to the doctor's digital wallet from the digital wallet of a third party, for example to promote use of telemedicine services to improve efficiency, efficacy of treatment, and/or reduce costs of treatment.

In some embodiments, the doctor module enables the doctor to add information to a patient's encrypted electronic health record. In some embodiments, the doctor module prompts the doctor to specify the patient's unique identifying information, a date and optionally time (either or both of which may be automatically specified by the doctor module without requiring manual input by the doctor), and health-related information to be added to the patient's encrypted electronic health record. The health-related information may include any health-related information including, without limitation: vital signs, diagnostic test results, images of the patient or a portion thereof (e.g., a photograph of a skin lesion or a radiographic image), a prescription for medication or therapeutic intervention, a record of a therapeutic intervention performed by the doctor, etc. The information added to the patient's encrypted electronic health record may be published to the blockchain ledger in the form of a block. In some embodiments, the blockchain computing system automatically grants access to the encrypted electronic health record block published to the blockchain ledger by the doctor without requiring the patient to specifically grant the doctor access to that block.

In some embodiments, the doctor module enables the doctor to sell products and/or services to a patient using the patient module. In some embodiments, the doctor module includes an electronic marketplace enabling the doctor to publish smart contracts to the blockchain ledger, each smart contract offering a product or service in exchange for payment with a blockchain token or other electronically transferrable valuable (e.g., a blockchain coupon, described in greater detail below). In some embodiments, the smart contract may require doctor approval (e.g., a prescription) before the smart contract is verified; in such embodiments, the blockchain computing system may transmit a request (e.g., via the doctor module acting as an inbound blockchain oracle) to a relevant doctor designated by the patient for such approval when the patient purchases the product or service offered in the smart contract. The relevant doctor may then approve the patient's purchase of the product or service by transmitting, through the doctor module acting as a blockchain input oracle, a request to the blockchain computing system to verify the smart contract, or alternatively may deny the patient's purchase of the product or service by either not transmitting the verification request to the blockchain computing system, or by affirmatively denying the patient's purchase of the product or service by transmitting a deny message through the doctor module (e.g., acting as an inbound blockchain oracle). In some embodiments, the blockchain computing system transmits a message to the patient, through the patient module, when the doctor approves or affirmatively denies the patient's purchase. When the smart contract is verified, the blockchain computing system transmits a message to the doctor (e.g., via the doctor module) to send the purchased product to the patient or to schedule an appointment (e.g., via a smart contract through the patient module) with the patient for the purchased service. In some embodiments, the appointment schedule request is automatically transmitted to the patient, without notifying the doctor, via the patient module upon verification of the smart contract (e.g., the patient's purchase of the offered service). In some embodiments, the product includes a sensor that provides health-related data to the patient module, and that may be stored in the patient's encrypted electronic health record or patient health record. In some embodiments, the product or service is travel to a destination that promotes health and wellness to visitors and/or provides healthcare-related services to visitors (e.g., "healthcare tourism" or "medical tourism").

In some embodiments, the doctor module is configured to enable a doctor to write a prescription for a patient. In some embodiments, the doctor module transmits the prescription to a third-party pharmacy; the third-party pharmacy receives the prescription using the third party module and fills the prescription for the patient. When the patient retrieves the filled prescription (e.g., by picking up the filled prescription or upon mailing of the filled prescription), the patient may receive an economic incentive (e.g., a token, or a blockchain coupon). In some embodiments, the economic incentive is specified in a smart contract published to the blockchain ledger by the doctor (e.g., using the doctor module) or the third party (e.g., a pharmacy or insurance provider using the third-party module). When the patient retrieves the filled prescription, the patient module or the third-party module may transmit a request to the blockchain computing system (e.g., acting as an inbound blockchain oracle) to execute the smart contract, whereupon the economic incentive is transferred to the patient's digital wallet. In some embodiments, an economic incentive is transferred to the prescribing doctor's digital wallet when the patient retrieves the filled prescription; in some such embodiments execution of the smart contract causes the economic incentive to be transferred from a third party's digital wallet (e.g., the digital wallet associated with the prescription drug/product's manufacturer or with an insurance company) to the doctor's digital wallet. In this manner, systems of the present disclosure can encourage prescription of medications or products that are on preferred formularies, are lower-cost alternatives to premium medications or products (e.g., generic drugs), etc. In some embodiments, a method of increasing patient adherence to a prescribed drug therapy comprises creating a smart contract providing an economic incentive to the patient upon retrieving (e.g., in person or by mail) a prescription written by a doctor using the doctor module; publishing, by the blockchain computing system, the smart contract; transmitting, by the patient module or by the third-party module (e.g., acting as an inbound blockchain oracle), a request to the blockchain computing system to execute the smart contract upon receipt of the prescription by the patient; and transferring, by the blockchain computing system, the economic incentive to the patient's digital wallet upon execution of the smart contract.

In some embodiments, the doctor module is configured to enable the doctor to submit an insurance claim to a third-party insurance provider, for example after the doctor performs a medical procedure for a patient whose medical care expenses are financially subsidized by the third-party insurance provider. In some embodiments, processing of the insurance claim is conducted via a smart contract. In such embodiments, a third-party (e.g., an insurance provider, a government agency, or a patient's employer) may publish its reimbursement amounts as smart contracts, with each smart contract specifying (at least) a medical service (e.g., by CPT code, by HCPCS code, by evaluation and management ("E&M") code, by ICD-10-CM diagnostic code, or by any other suitable coding system) and a reimbursement amount. In some embodiments, the smart contracts further comprise an in-network indicator that enables the smart contract creator to specify whether a particular smart contract includes a reimbursement amount for an in-network service provider (e.g., in-network doctor) or an out-of-network service provider (e.g., out-of-network doctor). Upon completion of a medical service for a patient whose medical care expenses are financially subsidized by the third-party (e.g., a third-party insurance provider), the doctor module transmits a request to the blockchain computing system (e.g., acting as an inbound blockchain oracle) to execute the smart contract associated with the medical service. The request may specify the medical service provided (e.g., by service code), patient identifying information (e.g., name and/or the patient's membership number with the third-party insurance provider), and optionally the cost of the medical service provided to the patient. Upon verification of the information included in the request, the blockchain computing system executes the smart contract, causing the blockchain computing system to transfer the reimbursement amount specified in the smart contract from the third party's digital wallet to the doctor's digital wallet. In some embodiments, the third party is a patient's employer, and execution of the smart contract causes the reimbursement amount specified in the smart contract to be transferred from the third-party employer's digital wallet to the doctor's digital wallet. In some embodiments, the third party is a government agency, and execution of the smart contract causes the reimbursement amount specified in the smart contract to be transferred from the third-party government agency's digital wallet to the doctor's digital wallet.

In some embodiments, the doctor module enables the doctor to communicate, anonymously or with attribution, with patients through the patient module, with other doctors using their doctor modules, and/or with third parties using the third-party module, to learn about and/or provide information about specific medical conditions, healthy activities, and the like.

In some embodiments, the doctor module is configured to enable a doctor to communicate via encrypted message (e.g., e-mail, text (SMS) or push notification) with a patient using the patient module, and/or with a third party using the third-party module. In some embodiments, the encrypted message is published to the blockchain ledger as a block with encryption such that only the sender of the encrypted message and the recipient of the encrypted message can access the text of the encrypted message. In some embodiments, the encrypted message is published to the blockchain ledger as a block with encryption to provide non-repudiation to the doctor and the patient.

In some embodiments, the doctor module is configured to enable a doctor to contribute media content (e.g., audio, video, and/or text) to be offered to patients, other doctors, and/or third parties through the patient module, the doctor module, and/or the third-party module (respectively), and to optionally receive an economic incentive (e.g., in the form of a blockchain token transferred to a digital wallet associated with the doctor) for contributing the media content and/or for views of the content by patients, by doctors, and/or by third parties.

In some embodiments, the doctor module is configured to enable the doctor to communicate with other doctors using their doctor modules to share non-confidential information about patients, best practices, and the like.

In some embodiments, the present disclosure provides a method of incentivizing a doctor to perform a task (e.g., perform an action or purchase a product or service), the method comprising: providing a blockchain computing system that stores and maintains a blockchain ledger, wherein the blockchain computing system hosts a smart contract that uses the blockchain ledger to verify blockchain transactions with the smart contract; providing an off-chain computer system comprising: a third-party module configured to enable a third party to generate a smart contract to incentivize a doctor to perform a task, wherein the smart contract is published to the blockchain ledger, a doctor module configured to enable the doctor to view a published smart contract; generating, by the doctor module or the third-party module, a request to execute the published smart contract; receiving, by the blockchain computing system, a request by the doctor to verify completion of the smart contract via a blockchain transaction; verifying, by the blockchain computing system, that the blockchain transaction satisfies the smart contract; and transferring, if the blockchain transaction satisfies the smart contract, a token, cryptocurrency, or a blockchain coupon to the doctor. In some embodiments, the blockchain coupon is a discount on a service offered by the third party or by the doctor. In some embodiments, the blockchain coupon is a token that is transferred to a digital wallet associated with the doctor. In some embodiments, the blockchain coupon is fiat currency. In some embodiments, the fiat currency is in the form of a discount off a cost of a service or a product offered by the third party or by the doctor. In some embodiments, the step of generating the request to execute the published smart contract is generated by the third-party module. In some embodiments, the step of generating the request to execute the published smart contract is generated by the doctor module. In some embodiments, the method further comprises transferring a token to a digital wallet associated with the third party before the step of transferring the financial reward to the doctor. In some embodiments, the method further comprises, upon redemption of the blockchain coupon by the doctor: transferring, from a digital wallet associated with the doctor, a purchase price to the third party; and transferring, from a digital wallet associated with the doctor or with the third party, a financial reward to an administrator of the blockchain computing system. In some embodiments, the financial reward comprises a value based at least in part on the purchase price. In some embodiments, the financial reward comprises a transaction fee. In some embodiments, the blockchain coupon is associated with an expiration date that temporally limits redemption of the blockchain coupon by a doctor.

Doctors can be incentivized to view educational videos provided by third parties. In some embodiments, a smart contract from the third party providing the educational video offers a blockchain token to the doctor for viewing the educational video. Once the patient views the video (e.g., via the off-chain patient module), the doctor module transmits a request to the blockchain computing system (e.g., acting as an inbound blockchain oracle) to execute the smart contract. Upon verification by the blockchain computing system that the doctor viewed the video, the blockchain computing system causes a blockchain token, a blockchain coupon, or cryptocurrency to the digital wallet of the doctor. As such, systems of the present disclosure may be used to conduct conveniently verified continuing education courses for doctors. Each of the foregoing modules may be a portion of a single computer program or mobile application, or may instead be provided as separate computer programs/mobile applications to the respective users. For example and without limitation, the patient module may be provided to the patient as a patient-specific mobile application, and may not include functionalities described herein that are featured in the doctor module or the third-party module.

In some embodiments, the present disclosure provides a computer-based method comprising: providing a blockchain computing system that stores and maintains a blockchain ledger, wherein the blockchain computing system hosts: (i) an encrypted electronic health record associated with a patient, and (ii) a smart contract that uses the blockchain ledger to verify blockchain transactions with the smart contract; providing an off-chain computer system comprising: a third-party module configured to enable a third party to generate a smart contract to incentivize a patient to complete a task (e.g., perform an action or purchase a product or service), wherein the smart contract is published to the blockchain ledger, a patient module configured to enable the patient to: (i) selectively grant access to at least a portion of the encrypted electronic health record associated with the patient to an authorized doctor, and (ii) generate a request to execute the smart contract, and a doctor module configured to enable the authorized doctor to: (i) access the encrypted electronic health record, and (ii) generate a request to publish a block to the blockchain ledger, wherein the block includes updated medical information about the patient; receiving, by the blockchain computing system, a request by the patient to verify completion of the smart contract via a blockchain transaction; verifying, by the blockchain computing system, that the blockchain transaction satisfies the smart contract; and transferring, if the blockchain transaction satisfies the smart contract, a blockchain token to a digital wallet associated with the patient. In some embodiments, the doctor module is configured to further enable the authorized doctor to: (iii) receive and transmit encrypted communications with the patient. In some embodiments, the doctor module is configured to further enable a doctor to: (iv) generate a smart contract to incentivize a patient to complete a task (e.g., perform an action or purchase a product or service), wherein the smart contract is published to the blockchain ledger. In some embodiments, the third-party module is configured to further enable the third party to offer a service to the patient and/or to a doctor. In some embodiments, the service is associated with a smart contract that is published to the blockchain ledger and, when completion by a patient or by a doctor is verified by the blockchain computing system, causes the blockchain computing system to transfer a blockchain token to a digital wallet associated with the patient or with the doctor. In some embodiments, the patient module is configured to further enable the patient to: (iii) receive and transmit encrypted communications with an authorized doctor. In some embodiments, the patient module is configured to further enable the patient to: (iv) receive and transmit encrypted communications with a second patient. In some embodiments, the patient module is configured to further enable the patient to: (v) perform a task associated with the smart contract. In some embodiments, the task is selected from the group consisting of: scheduling an appointment with a doctor, scheduling an appointment with a third party, participating in a telemedicine consultation with a doctor, purchasing a service from a third party, viewing a video published to the off-chain computer system by a doctor or by a third party, reading an article published to the off-chain computer system by a doctor or by a third party, completing a survey published to the off-chain computer system by a doctor or by a third party, publishing an inquiry to the off-chain computer system, and granting access to at least a portion of the encrypted electronic health record associated with the patient to a third party. In some embodiments, the third party is a pharmaceutical company, a hospital, a non-physician service provider, a healthcare tourism agency, a restaurant, a weight management vendor, a retailer, or a fitness center. In some embodiments, the method further comprises registering the smart contract with the off-chain computer system, wherein the step of registering comprises: sending, by the blockchain computing system, an address of the smart contract; creating, by the off-chain computer system, a smart contract token associated with the address of the smart contract; signing, by the off-chain computer system, the smart contract token upon completion of the task by the patient to create a signed token; and sending, by the off-chain computer system, the signed token to the blockchain computing system.

In some embodiments, the present disclosure provides a system comprising: a blockchain computing system configured to: (i) store and maintain a blockchain ledger, and (ii) host a smart contract that uses the blockchain ledger to verify blockchain transactions with the smart contract; and an off-chain computer system configured to: (i) receive a request from the blockchain computing system associated with the smart contract, (ii) enable a third party to generate a smart contract to incentivize a patient to complete a task (e.g., perform an action or purchase a product or service), wherein the smart contract is published to the blockchain ledger, (iii) enable the patient to: (a) selectively grant access to at least a portion of the encrypted electronic health record associated with the patient to an authorized doctor, and (b) generate a request to execute the smart contract, and (iv) enable the authorized doctor to: (a) access the encrypted electronic health record, and (b) generate a request to publish a block to the blockchain ledger, wherein the block includes updated medical information about the patient. In some embodiments, the off-chain computer system is further configured to enable the authorized doctor to: (c) receive and transmit encrypted communications with the patient. In some embodiments, the off-chain computer system is further configured to enable a doctor to: (d) generate a smart contract to incentivize a patient to complete a task (e.g., perform an action or purchase a product or service), wherein the smart contract is published to the blockchain ledger. In some embodiments, the off-chain computer system is further configured to enable the third party to offer a service to the patient and/or to a doctor. In some embodiments, the service is associated with a smart contract that is published to the blockchain ledger and, when completion by a patient or by a doctor is verified by the blockchain computing system, causes the blockchain computing system to transfer a blockchain token to a digital wallet associated with the patient or with the doctor. In some embodiments, the off-chain computer system is further configured to enable the patient to: (c) receive and transmit encrypted communications with an authorized doctor. In some embodiments, the off-chain computer system is further configured to enable the patient to: (d) receive and transmit encrypted communications with a second patient. In some embodiments, the off-chain computer system is further configured to enable the patient to: (e) perform a task associated with the smart contract. In some embodiments, the task is selected from the group consisting of: scheduling an appointment with a doctor, scheduling an appointment with a third party, participating in a telemedicine consultation with a doctor, purchasing a service from a third party, viewing a video published to the off-chain computer system by a doctor or by a third party, reading an article published to the off-chain computer system by a doctor or by a third party, completing a survey published to the off-chain computer system by a doctor or by a third party, publishing an inquiry to the off-chain computer system, and granting access to at least a portion of the encrypted electronic health record associated with the patient to a third party. In some embodiments, the third party is a pharmaceutical company, a hospital, a non-physician service provider, a healthcare tourism agency, a restaurant, a weight management vendor, a retailer, or a fitness center.

2. Blockchain Coupons

Health care providers (e.g., doctors, clinics, hospitals, etc.) and related non-clinical businesses struggle to incentivize patients to use products and services designed to improve patient health and/or maintain a patient's good health. Currently available blockchain platforms do not enable the use of blockchain coupons to reward consumer behavior with economic value (e.g., a blockchain token or discounts on purchases of products or services through a blockchain-driven marketplace).

The present disclosure provides blockchain coupons, in the form of automatically-executing smart contracts, that enable doctors or third-party businesses to provide economic incentives to health care consumers (e.g., patients).

In general, a blockchain coupon consistent with the present disclosure comprises a smart contract published to the blockchain ledger operated by the blockchain computing system. When the blockchain computing system verifies the blockchain coupon (e.g., upon purchase of a product or service by a patient through the patient module, or upon transfer of the blockchain coupon from a doctor via the doctor module or from a third party via the third-party module to the patient), transfers an economic incentive in the form of a blockchain token or a discount off of a purchase price of a product or service to be purchased at a later time through a marketplace associated with the blockchain computing system.

A blockchain coupon consistent with the present disclosure includes a financial value. In some embodiments, the financial value represents a discount off of a purchase price of a service or product available for purchase on a digital marketplace associated with the blockchain computing system. In some embodiments, the discount is represented in fiat cash. In other embodiments, the discount is represented as a percentage off of the purchase price. In other embodiments, the discount is represented by a token that may be redeemed towards the purchase price of another product or service offered on the digital marketplace.

In some embodiments, redeeming the blockchain coupon may provide the patient or the doctor with a token that includes a temporal restriction that limits use of the blockchain coupon (e.g., limits the type or identity or source/provider of the product(s) or service(s) with which the blockchain coupon might be used) for a specified amount of time. After the specified amount of time expires, the token may then be used to purchase any product or service through the electronic marketplace.

The blockchain coupon may specify a category of products or services (e.g., fitness tracking devices or therapeutic massage services or services offered by any healthcare provider on a specific insurance company's "in-network" provider list), for example as a condition of a smart contract associated with the blockchain coupon; redemption of the blockchain coupon is then restricted to products and services within the specified category(ies). In operation, the blockchain computing system verifies the smart contract associated with the blockchain coupon upon request by a patient only if, inter alia, the product or service desired by the patient includes a category-identifying string that matches a category-identifying string encoded in the smart contract associated with the blockchain coupon.

In some embodiments, the blockchain coupon specifies a specific product or service, for example as a condition of a smart contract associated with the blockchain coupon; redemption of the blockchain coupon is then restricted to the product or the service specified in the blockchain coupon. In operation, the blockchain computing system verifies the smart contract associated with the blockchain coupon upon request by a patient only if, inter alia, the product or service desired by the patient includes a product-identifying string that matches a product-identifying string encoded in the smart contract associated with the blockchain coupon.

In some embodiments, the blockchain coupon includes an expiration date that specifies a deadline or a period of time within which the patient must (i) purchase a product or service associated with the blockchain coupon, or (ii) complete a service associated with the blockchain coupon. The blockchain computing system verifies a smart contract associated with such blockchain coupons only if, inter alia, the purchase or completion of the service occurs by the specified deadline or within the specified time period. In some embodiments, the blockchain coupon provides one or more blockchain tokens; in such embodiments, the blockchain token may include a temporal restriction that limits the token's use to the purchase of products or services offered by the provider (e.g., the doctor or the third party) of the blockchain coupon. In some embodiments, the temporal restriction is a date after which use of the token is no longer restricted to use for products or services offered by the provider of the blockchain coupon.

To redeem a blockchain coupon, a patient selects a product or service from a digital marketplace associated with the blockchain computing system. When the patient completes the purchase transaction on the digital marketplace, the patient module transmits a response to the smart contract associated with the blockchain coupon (e.g., acting as an inbound blockchain oracle). The blockchain computing system verifies the response only if all of the required conditions of the smart contract are met (e.g., the product or service satisfies any category-specific or product-specific limitations specified in the smart contract; the purchase date and time are within date and time limitations that may be specified in the smart contract; and the patient's digital wallet includes economic value equal to or greater than—in view of the economic value of the blockchain coupon—the purchase price of the desired product or service). Upon verification, the blockchain computing system transfers an economic value in the form of a blockchain token, if required, and any economic value associated with the blockchain coupon from the patient's digital wallet to the seller of the product or service, and prompts the seller of the product or service to send the purchased product to the patient or schedule the service with the patient. In some embodiments, the blockchain coupon redeemed by the patient causes the blockchain computing system to transfer blockchain tokens (which may or may not include a temporal restriction and/or a use restriction) from the third party's digital wallet to the patient's digital wallet. In some embodiments, the step of scheduling the service with the patient automatically follows the step of transferring the economic value from the patient's digital wallet, for example by generating a smart contract published to the blockchain ledger that includes a scheduling offer specifying a date, a time, and a location of the service to be provided to the patient. Acceptance of the scheduling offer by the patient (e.g., via the patient module) comprises generating a response to the smart contract that is verified by the blockchain computing system if the response includes, inter alia, unique patient-identifying information that matches unique patient-identifying information specified in the scheduling offer smart contract.

In some embodiments, redeeming a blockchain coupon may require doctor approval (e.g., a prescription) before the smart contract is verified; in such embodiments, the blockchain computing system may transmit a request (e.g., via the doctor module acting as an inbound blockchain oracle) to a relevant doctor designated by the patient or by the blockchain coupon for such approval when the patient purchases the product or service specified in the blockchain coupon. The relevant doctor may then approve the patient's purchase of the product or service by transmitting, through the doctor module acting as an inbound blockchain oracle, a request to the blockchain computing system to verify the smart contract, or alternatively may deny the patient's purchase of the product or service by either not transmitting the verification request to the blockchain computing system, or by affirmatively denying the patient's purchase of the product or service by transmitting a deny message through the doctor module. In some embodiments, the blockchain computing system transmits a message to the patient, through the patient module, when the doctor approves or affirmatively denies the patient's purchase. When the smart contract is verified, the blockchain computing system transmits a message to the doctor (e.g., via the doctor module) to send the purchased product to the patient or to schedule an appointment (e.g., via a smart contract through the patient module) with the patient for the purchased service.

In some embodiments, the patient module is configured to enable the patient to search the blockchain ledger for published smart contracts associated with blockchain coupons that are specific to a disease, disorder, or health-related goal associated with the patient. For example, if a patient has a diagnosis of pre-diabetes (e.g., if the patient's encrypted electronic health record indicates that the patient has been diagnosed with pre-diabetes, or is at high risk of developing pre-diabetes, the patient module may enable the patient to search all published smart contracts that include blockchain coupons that (a) include a restriction on use for treating pre-diabetes or preventing or delaying onset of diabetes, and/or (b) do not include a restriction on use for treating or preventing a specific disease or disorder.

In an example method of use, a third party may purchase tokens for use as blockchain coupons from the blockchain computing system operator by transferring fiat cash to the blockchain computing system operator, causing the blockchain system operator to transfer tokens (or cryptocurrency) to the third party's digital wallet. The third party then generates a blockchain coupon, using the third-party module, that is published to the blockchain ledger in the form of a smart contract. In some embodiments, the third party transmits the tokens associated with the blockchain coupons to the digital wallet(s) associated with one or more patients, who are each notified of the receipt of the blockchain coupon via the patient module. If a patient purchases a product or service, or completes a service, that satisfies the smart contract associated with the blockchain coupon, the blockchain computing system transfers economic value (any combination of a blockchain token, cryptocurrency and valid blockchain coupons) from the patient's digital wallet to the third party's digital wallet, optionally less a transaction fee that may be transferred from the patient's digital wallet directly to the blockchain computing system operator's digital wallet.

In some embodiments, the blockchain computing system is configured to enable patients, using the patient module, to transfer a blockchain coupon to another patient, to a doctor using the doctor module, or to a third party using the third-party module, for example in exchange for a blockchain token, cryptocurrency or other economic value. As such, the blockchain computing system of the present disclosure may include a blockchain coupon digital marketplace whereby a patient possessing a blockchain coupon in his or her digital wallet may publish a smart contract to the blockchain ledger offering the blockchain coupon for sale or for trade to another user of the blockchain computing system (e.g., another patient using his or her own patient module, a doctor using the doctor module, or a third party using the third-party module). The blockchain computing system verifies the smart contract when another user transmits a response to the smart contract (e.g., acting as an inbound blockchain oracle) that includes, inter alia, offer information that matches the smart contract's sale price (e.g., a set economic value or a minimum economic value). Upon verification, the blockchain computing system causes the economic value offered by the other user (e.g., any combination of blockchain tokens, cryptocurrency, tokens, and other blockchain coupons) to transfer from the other user's digital wallet to the patient's digital wallet, and causes the blockchain coupon to transfer from the patient's digital wallet to the other user's digital wallet. In some embodiments, the blockchain computing system transfers a transaction fee (e.g., an economic value) from the digital wallet of the patient and/or the other user to the digital wallet of the blockchain computing system operator upon verification of the smart contract.

In some embodiments, the present disclosure provides a method of incentivizing a patient to perform a task, the method comprising: providing a blockchain computing system that stores and maintains a blockchain ledger, wherein the blockchain computing system hosts a smart contract that uses the blockchain ledger to verify blockchain transactions with the smart contract; providing an off-chain computer system comprising: a third-party module configured to enable a third party to generate a smart contract to incentivize a patient to perform a task, wherein the smart contract is published to the blockchain ledger, a patient module configured to enable the patient to view a published smart contract, and a doctor module configured to enable a doctor to: generate a smart contract to incentivize a patient to perform a task, wherein the smart contract is published to the blockchain ledger; generating, by the patient module, the third-party module or the doctor module, a request to execute the published smart contract; receiving, by the blockchain computing system, a request by the patient to verify completion of the smart contract via a blockchain transaction; verifying, by the blockchain computing system, that the blockchain transaction satisfies the smart contract; and transferring, if the blockchain transaction satisfies the smart contract, a blockchain coupon to the patient. In some embodiments, the blockchain coupon is a discount on a service offered by the third party or by the doctor. In some embodiments, the blockchain coupon is a token that is transferred to a digital wallet associated with the patient. In some embodiments, the blockchain coupon is fiat currency. In some embodiments, the fiat currency is in the form of a discount off a cost of a service or a product offered by the third party or by the doctor. In some embodiments, the step of generating the request to execute the published smart contract is generated by the patient module. In some embodiments, the step of generating the request to execute the published smart contract is generated by the third-party module. In some embodiments, the step of generating the request to execute the published smart contract is generated by the doctor module. In some embodiments, the method further comprises transferring a token to a digital wallet associated with the third party before the step of transferring the financial reward to the patient. In some embodiments, the method further comprises transferring a token to a digital wallet associated with the doctor before the step of transferring the financial reward to the patient. In some embodiments, the method further comprises, upon redemption of the blockchain coupon by the patient: transferring, from a digital wallet associated with the patient, a purchase price to the third party or to the doctor; and transferring, from a digital wallet associated with the doctor or with the third party, a financial reward to an administrator of the blockchain computing system. In some embodiments, the financial reward comprises a value based at least in part on the purchase price. In some embodiments, the financial reward comprises a transaction fee. In some embodiments, the blockchain coupon is associated with an expiration date that temporally limits redemption of the blockchain coupon by a patient.

In some embodiments, the present disclosure provides a method of incentivizing a doctor to perform a task, the method comprising: providing a blockchain computing system that stores and maintains a blockchain ledger, wherein the blockchain computing system hosts a smart contract that uses the blockchain ledger to verify blockchain transactions with the smart contract; providing an off-chain computer system comprising: a third-party module configured to enable a third party to generate a smart contract to incentivize a patient to perform a task, wherein the smart contract is published to the blockchain ledger, and a doctor module configured to enable a doctor to redeem a smart contract; generating, by the third-party module or the doctor module, a request to execute the published smart contract; receiving, by the blockchain computing system, a request by the doctor module or by the third-party module to execute the smart contract via a blockchain transaction; verifying, by the blockchain computing system, that the blockchain transaction satisfies the smart contract; and transferring, if the blockchain transaction satisfies the smart contract, a blockchain coupon to the doctor's digital wallet. In some embodiments, the blockchain coupon is a discount on a service offered by the third party or by the doctor. In some embodiments, the blockchain coupon is a token that is transferred to a digital wallet associated with the doctor. In some embodiments, the blockchain coupon is fiat currency. In some embodiments, the fiat currency is in the form of a discount off a cost of a service or a product offered by the third party or by a different third party. In some embodiments, the step of generating the request to execute the published smart contract is generated by the doctor module. In some embodiments, the step of generating the request to execute the published smart contract is generated by the third-party module. In some embodiments, the method further comprises transferring a token to a digital wallet associated with the third party before the step of transferring the financial reward to the doctor. In some embodiments, the method further comprises, upon redemption of the blockchain coupon by the doctor: transferring, from a digital wallet associated with the doctor, a purchase price to the third party; and transferring, from a digital wallet associated with the third party, a financial reward to an administrator of the blockchain computing system. In some embodiments, the financial reward comprises a value based at least in part on the purchase price. In some embodiments, the financial reward comprises a transaction fee. In some embodiments, the blockchain coupon is associated with an expiration date that temporally limits redemption of the blockchain coupon by a doctor.

In some embodiments, the present disclosure provides a blockchain coupon comprising: a financial value that represents a discount off of a purchase price of a service or product available for purchase on a blockchain computing system; and a request that, upon redemption by a patient, causes an off-chain computing system to verify a smart contract hosted by the blockchain computing system, wherein, upon verification of the smart contract, the smart contract causes transfer of the purchase price less the financial value from a digital wallet associated with the patient to a digital wallet associated with a provider of the service or product. In some embodiments, the blockchain coupon further comprises an expiration date that temporally limits redemption of the blockchain coupon by a patient. In some embodiments, the financial value represents a percent discount off of the purchase price. In some embodiments, the financial value represents a fixed fiat currency-based discount off of the purchase price. In some embodiments, the financial value is determined as a function of at least a time remaining until the expiration date. In some embodiments, the smart contract is further configured to cause, upon verification of the smart contract, transfer of a financial reward to the digital wallet associated with the patient. In some embodiments, the financial reward comprises a token. In some embodiments, the financial reward comprises fiat currency. In some embodiments, the financial reward comprises a second blockchain coupon comprising: a second financial value that represents a discount off of a purchase price of a second service or product available for purchase on the blockchain computing system; and a request that, upon redemption by a patient, causes the off-chain computing system to verify a second smart contract hosted by the blockchain computing system, wherein, upon verification of the second smart contract, the second smart contract causes transfer of the purchase price of the second service or product less the financial value from the digital wallet associated with the patient to the digital wallet associated with a provider of the service or product.

3. Tokenized Health Savings Accounts

Currently available Health Savings Accounts ("HSAs") strictly restrict consumers' purchasing choices, and wholly fail to incentivize a consumer for making purchasing choices that are beneficial health-wise or economically. In addition, employers who contribute to their employees' HSAs lack any real ability to influence their employees' health care spending behaviors through HSA subsidies. Currently available blockchain platforms similarly cannot influence consumers' health-related spending behaviors, and are not capable of hosting, monitoring or regulating consumers' purchasing choices with HSA funds.

The present disclosure provides a tokenized HSA on a blockchain computing system that provides these heretofore unavailable functions, and more.

In some embodiments, the tokenized HSA comprises a digital wallet (or a portion of a digital wallet) associated with a patient and configured to accept cryptocurrency, tokens, and/or fiat cash (e.g., contributions from employers or earned by patient behavior).

The token may be an HSA-specific token that includes an HSA identifier to prevent improper spending of the HSA-specific token on products and services that are not healthcare-related, or are not related to a disease, disorder, or health-related goal associated with the patient. For example, in embodiments wherein the token is an HSA-specific token, the digital marketplace associated with the blockchain computing system may require all smart contracts for purchasing a product or a service to include an HSA-eligibility string that the blockchain computing system compares to an HSA-specific token string during the step of verifying the smart contract associated with the patient's purchase of the product or service. If the smart contract includes an HSA-eligible string that indicates that HSA funds cannot be used to purchase the product or service associated with the smart contract, then the blockchain computing system will not verify the smart contract if the patient attempts to purchase the product or service using HSA-specific tokens. If the If the smart contract includes an HSA-eligible string that indicates that HSA funds can be used to purchase the product or service associated with the smart contract, then the blockchain computing system will verify the smart contract if, inter alia, the patient attempts to purchase the product or service using HSA-specific tokens and/or other blockchain tokens, cryptocurrency and/or blockchain coupons.

In some embodiments, a third party (e.g., an employer) or a doctor may offer an economic incentive (e.g., additional HSA tokens, blockchain tokens, cryptocurrency, or blockchain coupons) to patients who purchase products and/or services on the digital marketplace associated with the blockchain computing system that align with a disease, disorder, or health-related goal in the patient's encrypted electronic health record or patient health record. In some embodiments, the economic incentive is offered to the patient as a smart contract that may specify a product type or service category that must be purchased by the patient to earn the economic incentive. For example, to incentivize a patient to obtain a bone density assessment, a doctor using the doctor module, or a third party using the third-party module, may create a smart contract offering an economic incentive in the form of an HSA token if the patient purchases bone density assessment services through the digital marketplace associated with the blockchain computing system. A patient, using the patient module, may purchase bone density assessment services through the digital marketplace associated with the blockchain computing system, and the patient module may the transmit a response to the blockchain computing system (e.g., acting as an inbound blockchain oracle) requesting verification of the smart contract. If, inter alia, the purchased bone assessment service matches the service requirements of the smart contract, the blockchain computing system verifies the smart contract and causes the economic incentive (the HSA token in this example) to be transferred from the doctor's digital wallet to the patient's digital wallet.

In an example method of use, a third party (e.g., an employer) may purchase HSA tokens from the blockchain computing system operator by transferring (e.g., through the third-party module) fiat cash, blockchain tokens, or cryptocurrency to the blockchain computing system operator's digital wallet. An HSA-specific digital wallet (or a portion of a digital wallet) is established for a patient, for example by the third party or by the patient using the patient module. Patient-specific data (e.g., clinical, genomic, networked device data, and information from the patient's encrypted electronic health record) is gathered into the patient's electronic personal health record. The third party publishes one or more smart contracts to the blockchain ledger operated by the blockchain computing system; the smart contract(s) include a required task by the patient, such as purchasing a product or service through a digital marketplace associated with the blockchain ledger, or achieving a milestone change in one or more aspects of the patient-specific data, such as reducing the patient's resting heart rate by at least 5% or reducing the patient's $Hb_{A1c}$ level to less than 6.5%. The smart contract(s) also include an economic incentive payable to the patient upon satisfaction of the required task. When the patient satisfies the required task of a smart contract, the patient module transmits a response to the blockchain computing system (e.g., acting as an inbound blockchain oracle) requesting verification of the smart contract. If the response satisfies all conditions of the smart contract, the blockchain computing system verifies the smart contract and causes the economic incentive to be transferred from the third party's digital wallet to the patient's digital wallet. In some embodiments, the blockchain computing system also transfers a transaction fee (in blockchain tokens, cryptocurrency or fiat cash) from the third party to the blockchain computing system operator's digital wallet when the smart contract is verified.

In some embodiments, the present disclosure provides a method of incentivizing patient behavior, the method comprising: providing a blockchain computing system that stores and maintains a blockchain ledger, wherein the blockchain computing system hosts a smart contract that uses the blockchain ledger to verify blockchain transactions with the smart contract; providing an off-chain computer system comprising: a third-party module configured to enable a third party to generate a smart contract to incentivize a patient to perform a task, wherein the smart contract is published to the blockchain ledger, and a patient module configured to generate a request to execute the smart contract; generating, by the patient module, a request to execute the published smart contract; receiving, by the blockchain computing system, the request by the patient to verify completion of the smart contract via a blockchain transaction; verifying, by the blockchain computing system, that the blockchain transaction satisfies the smart contract; and transferring, if the blockchain transaction satisfies the smart contract, a health savings account token to a digital wallet associated with the patient. In some embodiments, the step of transferring the health savings account token comprises transferring the health savings account token from a digital wallet associated with the third party to the digital wallet associated with the patient. In some embodiments, the blockchain computing system is configured to further store a personal health record associated with the patient. In some embodiments, the personal health record includes at least one or more of: clinical data associated with the patient, genomic data associated with the patient, Internet of Things ("IoT") data associated with a device that is associated with the patient, and/or a health-related condition associated with the patient. In some embodiments, the off-chain computer system is configured to further store an electronic health record associated with the patient. In some embodiments, the electronic health record includes at least one or more of: demographic information associated with the patient, historical medical treatment data associated with the patient, scheduled medical treatment data associated with the patient, a medication prescription associated with the patient, an interventional plan associated with the patient, and/or IoT data associated with a device that is associated with the patient. In some embodiments, the task is associated with a health-related condition specified in the personal health record or with data specified in the electronic health record. In some embodiments, the task is selected from the group consisting of: a diagnostic test, compliance with a medication prescription, completion of an interventional plan, scheduling an appointment with a medical service provider, attending an appointment with a medical service provider, and attending an informational session. In some embodiments, the method further comprises transferring a health savings account token from the digital wallet associated with the patient if the blockchain transaction does not satisfy the smart contract. In some embodiments, the smart contract includes an expiration date for completion of the task, and wherein the step of transferring the health savings account token is not performed if the task is completed by the patient after the expiration date. In some embodiments, the step of transferring the health savings account token comprises: transferring an entire value of the health savings token to the digital wallet associated with the patient, if the step of transferring the entire value to the digital wallet associated with the patient would result in a total value of health savings account tokens in the digital wallet associated with the patient that does not exceed a predetermined maximum value, transferring a portion of the entire value of the health savings token to the digital wallet associated with the patient, if the step of transferring the entire value to the digital wallet associated with the patient would result in a total value of health savings account tokens in the digital wallet associated with the patient that exceeds the predetermined maximum value, and transferring no portion of the entire value of the health savings token to the digital wallet associated with the patient, if the digital wallet associated with the patient includes a total value of health savings account tokens in the digital wallet associated with the patient that is equal to the predetermined maximum value before completion of the task by the patient. In some embodiments, the predetermined maximum value is equal to a maximum value of health savings funds allowable under relevant law. In some embodiments, method further comprises transferring, from a digital wallet associated with the third party, a financial reward to an administrator of the blockchain computing system if the blockchain transaction satisfies the smart contract.

In some embodiments, the present disclosure provides a digital wallet comprising a health savings account token or fraction thereof.

4. Recruiting Medical Trial Participants Via Blockchain

Recruiting patients to participate in clinical studies is laborious, inefficient, and costly. Privacy regulations prevent clinical research organizations (e.g., private companies, hospitals or universities) from directly accessing large stockpiles of patient data that might otherwise streamline patient recruitment based on inclusion criteria and exclusion criteria. Currently, no accessible database enables clinical research organizations to easily recruit potential study participants without violating the strict privacy regulations such as the Health Insurance Portability and Accountability Act of 1996 ("HIPAA").

Systems and methods of the present disclosure enable a clinical research organization to efficiently identify potential study participants based on inclusion criteria and exclusion criteria, with substantially no risk of violating any potential study participant's privacy rights, and also enables clinical research organizations to reward or incentivize patients to participate in clinical research studies.

The blockchain computing system hosts (at least): (i) an encrypted electronic health record associated with each of a plurality of patients, and (ii) at least one smart contract that incentivizes patients to enable the clinical research organization to access a portion of the patient's encrypted electronic health record. In some embodiments, the portion of the patient's encrypted electronic health record includes at least the patient's age, gender, and country of residence. In some embodiments, the portion of the patient's encrypted electronic health record does not include any patient-identifying information (e.g., name, address, telephone number, e-mail address, etc.).

The smart contract may include study criteria (e.g., inclusion criteria and/or exclusion criteria) relevant to the clinical study. For example, if the clinical study required recruiting male patients aged 18-75 who have a body mass index ("BMI") of at least 30, normal $Hb_{A1c}$ levels (e.g., less than 6.5%), and who have not experienced a documented heart attack (e.g., myocardial infarction), the smart contract may include inclusion criteria of at least:

Gender=male,
Age=>17 and <76,
BMI≥30, and
$Hb_{A1c}$<6.5%;
and exclusion criteria of:
Patient's encrypted EHR includes documented heart attack.

The smart contract may also include an economic incentive, for example in the form of blockchain tokens, cryptocurrency, fiat cash, tokens (e.g., HSA tokens) or a blockchain coupon, payable to the patient if the patient meets all inclusion criteria and exclusion criteria in the smart contract and agrees to participate in the clinical study.

A patient wishing to enroll in a clinical study specified in the smart contract transmits (e.g., via the patient module acting as an inbound blockchain oracle) a request to the blockchain computing system to verify the smart contract. Upon verification, the blockchain computing system causes the economic incentive to transfer from the clinical research organization's digital wallet to the patient's digital wallet, and optionally further grants access to some or all of the remaining portion of the patient's encrypted electronic health record.

In some embodiments, individual patient data is not provided to the clinical research organization; in such embodiments the blockchain computing system provides anonymized patient data from the patients' encrypted electronic health records based on a query created by the contract research organization (e.g., using the third-party module) and published to the blockchain ledger by the blockchain computing system as a smart contract. In some embodiments, the blockchain computing system provides information obtained from a clinical decision support system ("CDSS") based on two or more components of a patient's encrypted electronic health record. In some embodiments, the blockchain computing system generates an output to the query based at least on CDSS information related to demographic, genomic, and/or Internet of Things ("IoT") data associated with a patient and information associated with the patient's encrypted electronic health record stored in the blockchain ledger and/or the patient's off-chain patient health record.

In some embodiments, the smart contract includes a patient compensation matrix that specifies an automatically varying economic incentive based on one or more patient compensation matrix factors. The patient compensation matrix factors may include any relevant factors that may incentivize patients to participate in a clinical study, especially in a clinical study for which recruiting suitable patients, or a suitable number of acceptable patients, may be or has proven to be difficult. In some embodiments, the patient compensation matrix factor is any one or more of: an elapsed time between publication of the smart contract to the blockchain ledger, a time remaining until an expiration date of the smart contract, a difference between a count of a maximum number of patients that may be enrolled in the medical study and a count of patients currently enrolled in the medical study, and/or a count of a number of the plurality of patients that satisfy the one or more study criteria. The patient compensation matrix may offer increasing economic incentives to patients the longer a smart contract has been published on the blockchain ledger, as the time to enroll in the clinical study approaches (e.g., as a recruitment time window specified in the smart contract approaches its end), as the number of remaining patient spots in the clinical study approaches zero, as the number of patients who satisfy all study criteria and verify the smart contract increases, or as the rate of patients who satisfy all study criteria and verify the smart contract decreases.

In some embodiments, the smart contract does not include an economic incentive. In such embodiments, the patient module enables the patient to receive a notification that he or she may satisfy all study criteria specified in a smart contract, and to transmit a request to the smart contract creator (e.g., the third-party clinical research organization) for a desired economic incentive. The request transmitted to the smart contract creator may be published to the blockchain ledger as a second smart contract; acceptance of the patient's economic incentive request by the third-party clinical research organization is then accomplished by the third party (e.g., using the third-party module) transmitting a response to the blockchain computing system (e.g., acting as an inbound blockchain oracle) to verify the second smart contract. Upon verification of the second smart contract, the blockchain computing system transfers the requested economic value from the third party's digital wallet to the patient's digital wallet, and optionally further grants access to some or all of the remaining portion of the patient's encrypted electronic health record.

In some embodiments, the third-party module enables a clinical research organization to query the encrypted electronic health records hosted by the blockchain computing system to determine, before publishing a patient recruitment smart contract to the blockchain ledger, whether proposed study criteria may yield a desirable number of clinical trial participants from among the plurality of patients whose encrypted electronic health records are hosted by the blockchain computing system. For example, if a clinical study will require 1,000 patients to achieve a desired study power value, the third-party module may enable the clinical research organization to propose study criteria (e.g., inclusion criteria and/or exclusion criteria) to determine how many patients participating in the blockchain computing system's encrypted electronic health record storage functionality have characteristics that meet those proposed study criteria. The blockchain computing system, upon receipt of the proposed study criteria from the third-party module, searches the encrypted electronic health records and provides to the third party a count of the number of encrypted electronic health records that satisfy all of the proposed study criteria in the query. In some embodiments, the blockchain computing system does not provide any direct access to a patient's encrypted electronic health record or to any individual patient's identifying information in response to such a query. Once the third-party clinical research organization finalizes the list of study criteria (e.g., based at least in part on the query(ies)), the third-party clinical research organization may publish a smart contract including the finalized study criteria to the blockchain ledger to begin recruitment of patients from among those associated with the blockchain computing system (e.g., patients using the patient module). In some embodiments, the third-party clinical research organization is not provided direct access to any patient's encrypted electronic health record or to any patient's identifying information upon publication of the smart contract. In some embodiments, the third-party clinical research organization is not provided direct access to any patient's encrypted electronic health record until the patient associated with the encrypted electronic health record affirmatively authorizes the blockchain computing system (e.g., via verification of a smart contract requesting direct access to the patient's encrypted electronic health record) to provide direct access to the patient's encrypted electronic health record to the third-party clinical research organization (e.g., via the third-party module).

In some embodiments, the third-party module enables a clinical research organization to create an operating model to test a clinical research hypothesis or return a probability of one or more predetermined responses from among the encrypted electronic health records associated with the blockchain computer system. In some embodiments, the operating model is only permitted to query the encrypted electronic health records associated with the blockchain computing system if running the operating model: (a) will not return information so specific that any patient associated with an encrypted electronic health record will be identifiable, and/or (b) will compensate the patients having encrypted electronic health records relevant to the operating model, for example by causing the blockchain computing system to transfer a blockchain token, cryptocurrency, and/or a blockchain coupon to each patient's digital wallet. In some embodiments, the operating model is deployed using the off-chain computing system. In some embodiments, responses to an operating model deployed using the off-chain computing system are published to the blockchain ledger by the blockchain computing system, for example for audit trail and/or non-repudiation purposes.

In some embodiments, the patient module is configured to enable a patient to specify a minimum economic incentive amount (e.g., a minimum number of blockchain tokens), as an opening bid in an auction format, that is required to prompt the patient to participate in a clinical research study. Across a plurality of patients using the patient module, a variety of minimum economic incentives (e.g., bids) may be specified. In such embodiments, the clinical research organization may offer increasing economic incentive amounts to the patients in an auction format until the number of accepting patients meets the clinical research organization's study needs. In some embodiments, each patient accepted by the clinical research organization receives the same economic incentive, for example the maximum economic incentive offered by the clinical research organization, even if that amount exceeds the patient's minimum economic incentive amount specified through the patient module. In some embodiments, the patient or group of patients receives the economic incentive amount upon enrollment in the clinical research study. In this manner, patient compensation for participating in clinical research studies may be optimized (e.g., maximized) and equitable between the study participants. In some embodiments, the auction for attracting patients to participate in the clinical study is operated off-chain, for example by the off-chain computing system, and the results of the auction process (e.g., an identifier of each patient accepting the economic incentive, the amount of the economic incentive, etc.) is published to the blockchain ledger as a block by the blockchain computing system.

In some embodiments, an enrollment smart contract is published to the blockchain ledger that, when verified, transfers an enrollment economic incentive (e.g., blockchain tokens, cryptocurrency, HSA tokens, or blockchain coupons) from the third-party clinical research organization's digital wallet to the patient's digital wallet. In such embodiments, the enrollment smart contract may only be satisfied if the patient has already satisfied all study criteria (e.g., in a recruitment smart contract previously verified) and completes an enrollment process (e.g., completes a first required task such as receiving a first dose of a study drug/placebo or receiving an initial study procedure/placebo procedure). In some embodiments, the patient module transmits a request to the blockchain computing system (e.g., acting as an inbound blockchain oracle) to verify the enrollment smart contract upon, for example, the patient "checking in" to the first required task. In some embodiments, the third-party module transmits the request to the blockchain computing system (e.g., acting as an inbound blockchain oracle) to verify the enrollment smart contract when the third-party clinical research organization records study data associated with the patient and with the first required task to a computing device associated with the blockchain computing system.

In some embodiments, a study completion smart contract is published to the blockchain ledger that, when verified substantially as described elsewhere herein, transfers a study completion economic incentive (e.g., blockchain tokens, cryptocurrency, HSA tokens, or blockchain coupons) from the third-party clinical research organization's digital wallet to the patient's digital wallet. In such embodiments, the study completion smart contract may only be satisfied if the patient has completed all required tasks (e.g., receiving the last dose of a study drug or attending the last scheduled patient assessment appointment specified in a clinical research plan). In some embodiments, the patient module transmits a request to the blockchain computing system (e.g., acting as an inbound blockchain oracle) to verify the study completion smart contract upon, for example, the patient "checking in" to the last required task. In some embodiments, the third-party module transmits the request to the blockchain computing system (e.g., acting as an inbound blockchain oracle) to verify the study completion smart contract when the third-party clinical research organization records study data associated with the patient and with the last required task to a computing device associated with the blockchain computing system.

In some embodiments, the present disclosure provides a method of recruiting patients for a medical study, the method comprising: providing a blockchain computing system that stores and maintains a blockchain ledger, wherein the blockchain computing system hosts: (i) an encrypted health record associated with each of a plurality of patients, and (ii) a smart contract that uses the blockchain ledger to verify blockchain transactions with the smart contract; providing an off-chain computer system comprising: a third-party module configured to enable a third party to generate a smart contract to incentivize a patient to complete a task (e.g., perform an action or purchase a product or service), wherein the smart contract is published to the blockchain ledger, and a patient module configured to enable the patient to: (i) selectively grant access to at least a portion of the encrypted health record associated with the patient to the third party, and (ii) generate a request to execute the smart contract; receiving, by the blockchain computing system, a request by the patient to verify completion of the smart contract via a blockchain transaction; verifying, by the blockchain computing system, that the blockchain transaction satisfies the smart contract; and transferring, if the blockchain transaction satisfies the smart contract, a blockchain token to a digital wallet associated with the patient. In some embodiments, the third-party module is further configured to: enable the third party to provide one or more study criteria associated with the medical study; enable the third party to specify an initial value of the blockchain token to be transferred to the digital wallet associated with the patient if the blockchain transaction satisfies the smart contract; display, to the third party, a count of a number of the plurality of patients that satisfy the one or more study criteria; and not display any portion of the encrypted health record to the third party before the step of transferring the blockchain token to the digital wallet associated with the patient. In some embodiments, the patient module is further configured to: display, to the patient, an invitation to view study criteria associated with the medical study; display, to the patient, a value of an initial blockchain token to be transferred to the digital wallet associated with the patient if the blockchain transaction satisfies the smart contract; and enable the patient to enroll in the medical study by selectively granting access to at least a portion of the encrypted health record associated with the patient to the third party. In some embodiments, the patient module is further configured to enable the patient to offer a second value of the blockchain token to the third party to induce the patient to enroll in the medical study, and wherein the third-party module is further configured to enable the third party to accept or reject the second value offer by the patient. In some embodiments, the third-party module is further configured to: enable the third party to specify a modified value of the blockchain token to be transferred to the digital wallet associated with the patient if the blockchain transaction satisfies the smart contract, wherein the modified value of the blockchain token is greater than the initial value of the blockchain token. In some embodiments, the smart contract includes an operating model comprising one or more of: the study criteria, a count of a minimum number of patients desired to be enrolled in the medical study, and/or a count of a maximum number of patients that may be enrolled in the study. In some embodiments, the operating model comprises a statistical model, a probabilistic mathematical model, or an algorithm that, when executed by the off-chain computing system, causes the return a probability of one or more predetermined responses from among the encrypted electronic health records associated with the blockchain computer system. In some embodiments, the study criteria include at least one inclusion criterion. In some embodiments, the study criteria include at least one exclusion criterion. In some embodiments, the smart contract includes a patient compensation matrix comprising: the initial value of the blockchain token to be transferred to the digital wallet associated with the patient if the blockchain transaction satisfies the smart contract; and a modified value of the blockchain token to be transferred to the digital wallet associated with the patient if the blockchain transaction satisfies the smart contract, wherein the modified value of the blockchain token is calculated as a function of at least: (i) the initial value of the blockchain token, and (ii) a patient compensation matrix factor. In some embodiments, the patient compensation matrix factor includes any one or more of: an elapsed time between publication of the smart contract to the blockchain ledger, a time remaining until an expiration date of the smart contract, a difference between a count of a maximum number of patients that may be enrolled in the medical study and a count of patients currently enrolled in the medical study, and/or a count of a number of the plurality of patients that satisfy the one or more study criteria. In some embodiments, the method further comprises transferring, from a digital wallet associated with the third party, a financial reward to an administrator of the blockchain computing system if the blockchain transaction satisfies the smart contract.

5. Stable Healthcare Blockchain Tokens

Cryptocurrencies are generally characterized by volatile valuations and little stability. That volatility and instability creates a barrier to adoption by a stable industry (e.g., health care services) despite any advantages in privacy, efficiency, and free market choice for patients.

The present disclosure provides a stable blockchain token having a value tied to the value of a stable fiat currency (or two or more fiat currencies), or to the value of a stable cryptocurrency (or two or more cryptocurrencies). In addition, stability of the blockchain token may be increased by limiting or controlling the number of blockchain tokens available for use with the blockchain computing system.

Stable blockchain tokens of the present disclosure are assigned a value equal to a mathematical combination (e.g., multiple) of: (i) the value of a predetermined currency or predetermined combination of currencies; and (ii) a predetermined scaling factor. For stability sufficient to be suitable for use in a stable industry, such as health care services, the currency(ies) must be predetermined (that is, fixed and generally not replaced other than in extraordinary circumstances such as extreme devaluation of the predetermined currency). Similarly, for stability sufficient to be suitable for use in a stable industry, such as health care services, the scaling factor must also be predetermined.

In some embodiments, the currency is a fiat currency (e.g., a stable fiat currency), such as the United States Dollar, the Euro, the British Pound Sterling, the Japanese Yen, or the Chinese Yuan. In some embodiments, the currency is more than one fiat currency (e.g., an average or weighted average of two or more fiat currencies), such as any two or more of: the United States Dollar, the Euro, the British Pound Sterling, the Japanese Yen, and the Chinese Yuan.

In other embodiments, the currency is a cryptocurrency or more than one cryptocurrency (e.g., an average or weighted average of two or more cryptocurrencies), such as Bitcoin, Ethereum, Zcash, Dash, Ripple, Monero, Bitcoin Cash, NEO, Cardano, and/or EOS. Although none of these cryptocurrencies may be, individually, stable enough for use in a stable industry (e.g., health care services) at the time of this invention, a mathematical combination of two or more crytpocurrencies may provide suitable stability in the value of the stable blockchain token over time.

In some embodiments, the predetermined currency is a mathematical combination (e.g., average) of one or more fiat currencies (e.g., the United States Dollar) and one or more cryptocurrencies (e.g., Ethereum).

The predetermined scaling factor can be any positive number, including an ordinal number (e.g., 1), a positive fraction (e.g., ⅞), a positive rational number, or a positive irrational number (e.g., π). In some embodiments, the predetermined scaling factor is 1.

The stable blockchain token enables users of a blockchain computing system featuring the stable blockchain token to create effective economic incentives (e.g., in the form of smart contracts) to persuade other users of the blockchain computing system to perform desirable tasks (e.g., purchase a product or service). For example, a third party using the third-party module described herein may publish a smart contract to the blockchain ledger that, when verified, causes the stable blockchain token to be transferred from the third party's digital wallet to the other user's (e.g., the patient's) digital wallet. The smart contract may require performance of a task by the other user (e.g., patient) to enable the blockchain computing system to verify the smart contract. For example, to incentivize a patient to increase her knowledge about long-term health risks associated with smoking, a third party may publish (e.g., via the third-party module) a smart contract to the blockchain ledger that requires the patient to view a video featuring information about long-term health risks associated with smoking in order to receive the stable blockchain token from the third party. In operation, publication of the smart contract to the blockchain ledger prompts the patient to elect to view the required video (e.g., via the patient module). Upon completion of the task, in this case viewing the required video, the patient module transmits a request to the blockchain computing system (e.g., acting as an inbound blockchain oracle) to verify the smart contract. If the request includes, inter alia, information matching the smart contract's required task(s) (e.g., that the patient viewed the video to completion), the blockchain computing system verifies the smart contract and causes transfer of the stable blockchain token from the third party's digital wallet to the patient's digital wallet.

The stable blockchain token may be used to purchase products or services on a digital marketplace associated with the blockchain computing system.

The stable blockchain tokens may be transferred from one user (e.g., patient) to another user (e.g., another patient).

In some embodiments, the present disclosure provides a stable healthcare blockchain token, wherein one healthcare blockchain token comprises a value directly proportional to a value of one unit of a predetermined fiat currency. In some embodiments, the value of the one healthcare blockchain token is equal to a multiple of (i) the value of the one unit of the predetermined fiat currency, and (ii) a predetermined scaling factor. In some embodiments, the scaling factor is 1. In some embodiments, the one unit of the predetermined fiat currency is 1 United States Dollar. In some embodiments, the one unit of the predetermined fiat currency is 1 Euro. In some embodiments, the one unit of the predetermined fiat currency is 1 British Pound Sterling. In some embodiments, the one unit of the predetermined fiat currency is 1 Japanese Yen. In some embodiments, the one unit of the predetermined fiat currency is 1 Chinese Yuan. In some embodiments, the healthcare blockchain token consists essentially of a value directly proportional to the value of one unit of the predetermined fiat currency. In some embodiments, the healthcare blockchain token consists of a value directly proportional to the value of one unit of the predetermined fiat currency. In some embodiments, the healthcare blockchain token consists of a value of one unit of a combination of predetermined fiat currencies.

In some embodiments, the present disclosure provides a stable healthcare blockchain token, wherein one healthcare blockchain token comprises a value directly proportional to a value of one unit of a predetermined cryptocurrency. In some embodiments, the value of the one healthcare blockchain token is equal to a multiple of (i) the value of the one unit of the predetermined cryptocurrency, and (ii) a predetermined scaling factor. In some embodiments, the scaling factor is 1. In some embodiments, the one unit of the predetermined cryptocurrency is selected from the group consisting of: 1 Bitcoin, 1 Ethereum, 1 Zcash, 1 Dash, 1 Ripple, 1 Monero, 1 Bitcoin Cash, 1 NEO, 1 Cardano, and 1 EOS. In some embodiments, the one unit of the predetermined cryptocurrency is an average value of 1 Ethereum and 1 unit of each of at least one additional cryptocurrency.

In some embodiments, the present disclosure provides a method of incentivizing behavioral choices of a patient, the method comprising transferring to a digital wallet associated with the patient a stable healthcare blockchain token as disclosed herein upon verification of a smart contract, wherein: the smart contract uses a blockchain ledger to verify blockchain transactions with the smart contract; and verification of the smart contract comprises: receiving, by a blockchain computing system configured to host the smart contract, a request by the patient to verify completion of the smart contract via a blockchain transaction, and verifying, by the blockchain computing system, that the blockchain transaction satisfies the smart contract. In some embodiments, completion of the smart contract requires the patient to perform a health-related task. In some embodiments, the task is selected from the group consisting of: scheduling an appointment with a doctor, scheduling an appointment with a third party, participating in a telemedicine consultation with a doctor, purchasing a service from a third party, viewing a video published to the off-chain computer system by a doctor or by a third party, reading an article published to the off-chain computer system by a doctor or by a third party, completing a survey published to the off-chain computer system by a doctor or by a third party, publishing an inquiry to the off-chain computer system, and granting access to at least a portion of the encrypted electronic health record associated with the patient to a third party.

In some embodiments, the present disclosure digital wallet associated with a patient, wherein the digital wallet comprises a stable healthcare blockchain token as disclosed herein.

What is claimed is:

1. A computer-based method comprising:
   providing a blockchain computing system that stores and maintains a blockchain ledger, wherein the blockchain computing system hosts: (i) an encrypted electronic health record associated with a patient, and (ii) a smart contract that uses the blockchain ledger to verify blockchain transactions with the smart contract;
   providing an off-chain computer system comprising:
      a third-party module configured to enable a healthcare provider to generate a smart contract to incentivize a patient to complete a task, purchase a product, or purchase and receive a service, wherein the smart contract is published to the blockchain ledger,
      a patient module configured to enable the patient to: (i) selectively grant access to at least a portion of the encrypted electronic health record associated with the patient to an authorized doctor, (ii) generate a request to execute the smart contract, and (iii) perform a task associated with the smart contract, and
      a doctor module configured to enable the authorized doctor to: (i) access the encrypted electronic health record, and (ii) generate a request to publish a block to the blockchain ledger, wherein the block includes updated medical information about the patient;
   receiving, by the blockchain computing system, a request by the patient to execute the smart contract via a blockchain transaction;
   verifying, by the blockchain computing system, that the blockchain transaction satisfies the smart contract; and
   transferring, if the blockchain transaction satisfies the smart contract, a blockchain token to a digital wallet associated with the patient, wherein the patient module is configured to further enable the patient to: (v) perform a task associated with the smart contract, and wherein the task is selected from the group consisting of: scheduling an appointment with a healthcare provider, attending a scheduled appointment with a healthcare provider, participating in a telemedicine consultation with a healthcare provider, viewing a video published to the off-chain computer system, reading an article published to the off-chain computer system, completing a survey published to the off-chain computer system, publishing an inquiry to the off-chain computer system, granting access to at least a portion of the encrypted electronic health record associated with the patient, retrieving a purchased prescribed medication, retrieving a prescribed test, receiving a prescribed treatment, playing a sponsored game, and applying to participate in a clinical study.

2. The computer-based method of claim 1, wherein the product to be purchased is a health-related product.

3. The computer-based method of claim 2, wherein the health-related product is a health monitoring device, an over-the-counter medication, a prescribed pharmaceutical, an exercise device, a health club membership, an orthopedic product, or a healthy food.

4. The computer-based method of claim 1, wherein the service to be purchased and received is related to improving or maintaining the patient's health.

5. The computer-based method of claim 1, wherein the authorized healthcare provider is a clinical research organization, and wherein the task is applying to participate in a clinical study associated with the clinical research organization.

6. The computer-based method of claim 5, wherein the step of enabling the patient to selectively grant access to the portion of the encrypted electronic health record associated with the patient includes granting access to the patient's age, gender, and country of residence.

7. The computer-based method of claim 6, wherein the step of enabling the patient to selectively grant access to the portion of the encrypted electronic health record associated with the patient does not include granting access to the patient's patient-identifying information including the patient's name, address, telephone number, or email address.

8. The computer-based method of claim 5, wherein the patient module is further configured to enable the patient to (i) accept an incentive offered by the contract research organization for the patient to enroll in the clinical study, or (ii) request an increased incentive from the contract research organization to enroll in the clinical study.

9. A system comprising:
   a blockchain computing system configured to:
      (i) store and maintain a blockchain ledger, and
      (ii) host a smart contract that uses the blockchain ledger to verify blockchain transactions with the smart contract; and
   an off-chain computer system configured to:
      (i) receive a request from the blockchain computing system associated with the smart contract,
      (ii) enable an authorized healthcare provider to generate a smart contract to incentivize a patient to complete a task, purchase a product, or purchase and receive a service, wherein the smart contract is published to the blockchain ledger,
      (iii) enable the patient to: (a) selectively grant access to at least a portion of the encrypted electronic health record associated with the patient to the authorized healthcare provider, and (b) generate a request to execute the smart contract, and (iv) enable the authorized healthcare provider to: (a) access the encrypted electronic health record, and (b) generate a request to publish a block to the blockchain ledger, wherein the block includes updated medical information about the patient, wherein the task is selected from the group consisting of: scheduling an appointment with the authorized healthcare provider or with a second healthcare provider, attending a scheduled appointment with the authorized healthcare provider or with a second healthcare provider, participating in a telemedicine consultation with the authorized healthcare provider or with a second healthcare provider, viewing a video published to the off-chain computer system, reading an article published to the off-chain computer system, completing a survey published to the off-chain computer system, publishing an inquiry to the off-chain computer system, granting access to at least a portion of the encrypted electronic health record associated with the patient, retrieving a purchased prescribed medication, retrieving a prescribed test, receiving a prescribed treatment, playing a sponsored game, and applying to participate in a clinical study.

10. The system of claim 9, wherein the product to be purchased is a health-related product.

11. The system of claim 10, wherein the health-related product is a health monitoring device, an over-the-counter medication, a prescribed pharmaceutical, an exercise device, a health club membership, an orthopedic product, or a healthy food.

12. The system of claim 9, wherein the service to be purchased and received is related to improving or maintaining the patient's health.

13. The system of claim 9, wherein the authorized healthcare provider is a clinical research organization, and wherein the task is applying to participate in a clinical study associated with the clinical research organization.

14. The system of claim 13, wherein the off-chain computer system is further configured to enable the patient to selectively grant access to the portion of the encrypted electronic health record associated with the patient includes granting access to the patient's age, gender, and country of residence.

15. The system of claim 14, wherein the off-chain computer system is further configured to enable the patient to selectively grant access to the portion of the encrypted electronic health record associated with the patient without granting access to the patient's patient-identifying information including the patient's name, address, telephone number, or email address.

16. The system of claim 13, wherein the off-chain computer system configured to enable the patient to (i) accept an incentive offered by the contract research organization for the patient to enroll in the clinical study, or (ii) request an increased incentive from the contract research organization to enroll in the clinical study.

* * * * *